(12) United States Patent
Tyagi et al.

(10) Patent No.: US 7,332,340 B2
(45) Date of Patent: Feb. 19, 2008

(54) PROCESS FOR IDENTIFYING A NOVEL TARGET FOR USE FOR THE DEVELOPMENT OF THERAPEUTIC MODALITIES AND DRUGS EFFECTIVE AGAINST TUBERCULOSIS

(75) Inventors: Jaya Sivaswami Tyagi, New Delhi (IN); Vandana Kapur, New Delhi (IN)

(73) Assignee: The Director, All India Institute of Medical Science, New Delhi (IN)

( * ) Notice: Subject to any disclaimer, the term of this patent is extended or adjusted under 35 U.S.C. 154(b) by 336 days.

(21) Appl. No.: 10/415,827

(22) PCT Filed: Feb. 8, 2002

(86) PCT No.: PCT/IN02/00022

§ 371 (c)(1),
(2), (4) Date: Oct. 3, 2003

(87) PCT Pub. No.: WO03/066838

PCT Pub. Date: Aug. 14, 2003

(65) Prior Publication Data

US 2005/0214754 A1 Sep. 29, 2005

(51) Int. Cl.
*C12N 15/74* (2006.01)
*A61K 39/04* (2006.01)
*C12Q 1/00* (2006.01)
*C12Q 1/68* (2006.01)
*C12Q 1/02* (2006.01)

(52) U.S. Cl. ........................ 435/471; 424/248.1; 435/4; 435/6; 435/29; 435/40.5; 435/41; 435/69.1; 435/440; 536/23.1; 536/23.7

(58) Field of Classification Search ............. 424/248.1; 435/4, 6, 29, 40.5, 41, 69.1, 44, 471, 440; 536/23.1, 23.7
See application file for complete search history.

(56) References Cited

OTHER PUBLICATIONS

Saini, D.K., et al. Microbiology(Reading), vol. 150, No. part 4, pp. 865-875, Apr. 2004.*
Park, H.-D., et al. Molecular Microbiology, vol. 48, No. 3, pp. 833-843, May 2003.*
Malhotra, V., et al. FEMS Microbiology Letters, vol. 231, No. 2, pp. 237-245, Feb. 2004.*

* cited by examiner

*Primary Examiner*—Rodney P Swartz
(74) *Attorney, Agent, or Firm*—Venable LLP; Marina V. Schneller

(57) ABSTRACT

The present invention relates to a process for identifying a novel target for use for the development of therapeutic modalities and drugs effective against tuberculosis comprising testing *M. tuberculosis* devR mutant strain for virulence in guinea pigs.

5 Claims, 4 Drawing Sheets

FIG. 2A
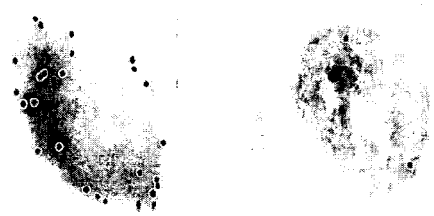
FIG. 2B-1          FIG. 2B-2
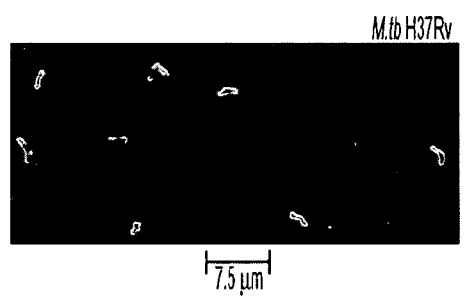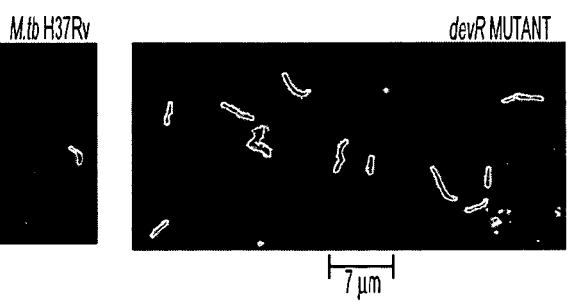
FIG. 2C

PROCESS FOR IDENTIFYING A NOVEL TARGET FOR USE FOR THE DEVELOPMENT OF THERAPEUTIC MODALITIES AND DRUGS EFFECTIVE AGAINST TUBERCULOSIS

This invention relates to a process for identifying a novel target for use for the development of therapeutic modalities and drugs effective against tuberculosis. Specifically, this invention relates to a process for identifying new and novel targets for the development of therapeutic modalities including anti tubercular drugs with special reference to mycobacterial existence persistence in hypoxia.

Tuberculosis is the leading cause of death from a single infectious agent killing more than 3 million people per year worldwide. In the year 1998, the estimated number of TB cases in India was 2,078,076 among which 935,134 cases were likely to be infectious. The consequence of infection is clearly an outcome of the continuous interplay between the pathogen and the host immune defense. In most instances, the infected individual mounts an effective immune response that culminates in granuloma formation around the effective foci and cessation of disease progression. The environment within granulomas is predicted to be hypoxia. Clinical studies suggest that the bacilli within these granulomas are not killed but instead remain dormant. This is termed a latent infection. Approximately 10% of latent infections reactivate, resulting in active infectious disease months to years after initial infection. The large number of latently infected individuals presents a major impediment to reducing the incidence of tuberculosis and the rate of M. tuberculosis transmission. The adaptation of M. tuberculosis during the spectrum of infection and disease is likely implemented through precise genetic pathways that are modulated by specific physiological and environmental conditions within host tissues.

There is an urgent need to understand these pathways in order to devise novel and more directed strategies for the prevention, control and treatment of tuberculosis. Conventional drugs target pathways required for bacterial growth and division such as cell-wall biosynthesis and DNA replication. Their poor activity against slow-growing or non-growing bacteria is thought to be an important reason why currently used regimens take so long to eradicate infection.

The devR-devS genes, designated as Rv3133c and Rv3132c respectively in the annotated M. tuberculosis genome are predicted to encode a response regulator, DevR, and a histidine kinase sensor, DevS, respectively. This genetic system was identified earlier in our laboratory by subtractive hybridization using RNA from virulent and avirulent strains of M. tuberculosis. Here we describe the process of identifying this system as a new and novel target for the development of therapeutic modalities including anti tubercular drugs with special reference to mycobacterial persistence existence in hypoxia.

Therefore the main object of the invention is to identify the target which is responsible for the recurrence/reactivation of the disease in the patient or that which enables the organism to adapt to hypoxia.

Another object of this invention is to identify the target responsible for the recurrence/reactivation of the disease or that which enables the organism to adapt to hypoxia and to develop the therapeutic modalities and anti tubercular drugs.

SUMMARY OF THE INVENTION

According to this invention there is provided a process for identifying a novel target for use for the development of therapeutic modalities and drugs effective against tuberculosis comprising:

I. disrupting devR (Rv3133c) gene located in a ~3.3 kb EcoRI-HindIII insert of plasmid pJT53.34 with kanamycin resistance $Km^R$ cassette,
II. constructing pJQ200SkdevR::kan from the disrupted devR gene,
III. introducing said plasmid into M. tuberculosis H37Rv by electroporation,
IV. selecting single crossover transformants indicative of plasmid integration on middle brook 7H10 agar plates containing 20 µg/ml kanamycin,
V. analyzing the same by polymerase chain reaction (PCR) for the presence of devR, $Km^R$ and sucrose resistance SacB gene sequences,
VI. subjecting said sequences to the step of Southern analysis with devR probe, devS probe kanamycin resistant gene probe so as to designate M. tuberculosis Dup devR containing wild-type and the disrupted copies of the devR locus,
VII. growing M. tuberculosis Dup devR in Middlebrook 7H9 medium containing kanamycin 20 µg/ml and 2% sucrose for 7 days,
VII. subjecting said grown M. tuberculosis Dup devR strain into a plurality of plates having a Middlebrook 7H10 medium containing kanamycin 20 µg/ml and 2% sucrose therein so as to obtain kanamycin resistant transformants,
XI. subjecting said grown M. tuberculosis devR to the step of Southern hybridization followed by polymerase chain reaction process for the confirmation of said allelic exchange,
X. subjecting said transformants to the step of polymerase chain reaction analysis for devR::kan disrupted gene,
XI. subjecting said devR::kan disrupted gene to the step of Western blotting and immuno electron microscopy for the confirmation of functional disruption of said gene,
XII. evaluating the viability of growth of the strain M. tuberculosis devR mutant under conditions of oxygen limitation for devR and devS gene expression,
XIII. evaluating the growth and viability of said. strain M. tuberculosis devR mutant under conditions of oxygen limitation in aerobic conditions for devR and devS gene expression,
XIV. subjecting said grown strain to the step of RT-PCR analysis for transcripts obtained from the Rv3134c-devR-devS operon,
XV. scanning said transcripts by using the Ultra-Violet products gel documentation system and subjecting the same to the step of densitometric analysis by using a computer software,
XVI. testing M. tuberculosis devR mutant strain for virulence in guinea pigs.

DESCRIPTION OF THE DRAWINGS

The process for identifying a novel target for use for the development of therapeutic modalities and drugs effective against tuberculosis is herein described in detail with the help of the accompanying drawings wherein.

b) PCR analysis of a representative devR mutant clone.

Figure 1:
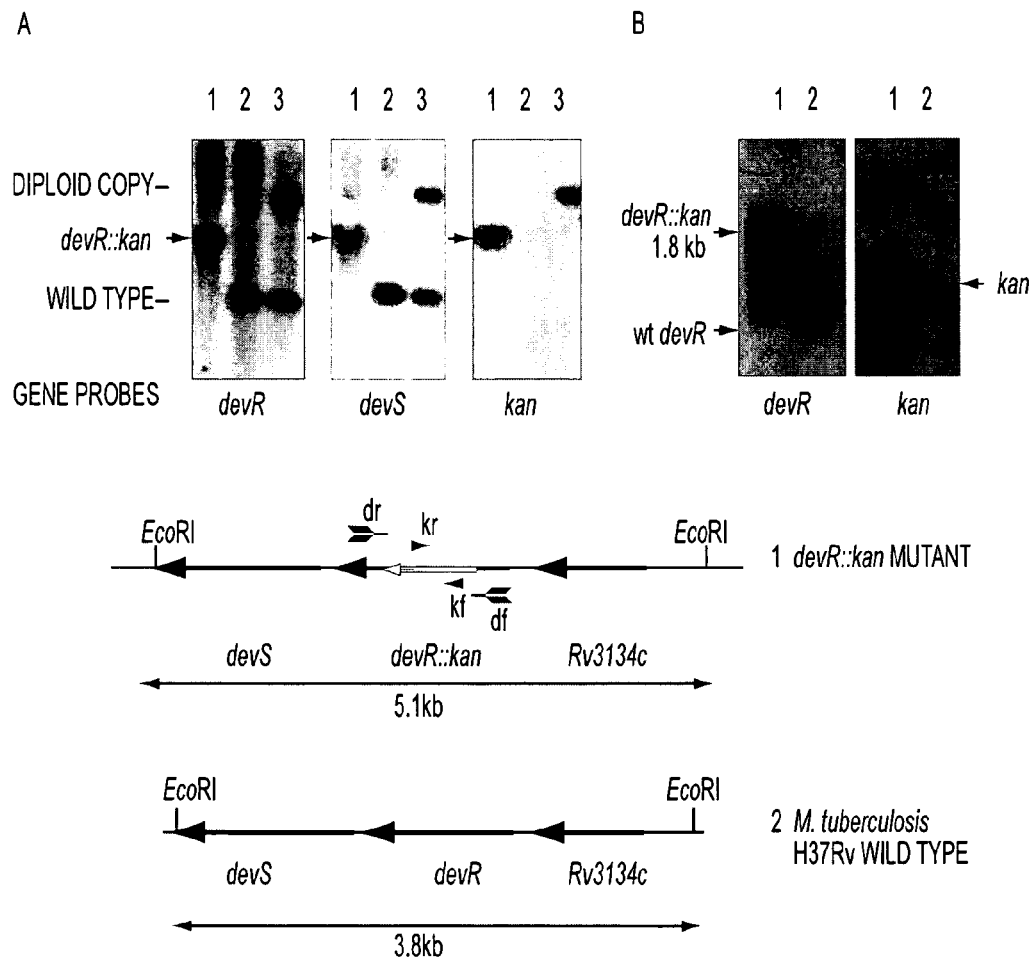
FIG. 1 shows the construction of devR mutant strain of M. tuberculosis
a) Southern hybridization analysis of recombinant M. tuberculosis strains.
Figure 3:
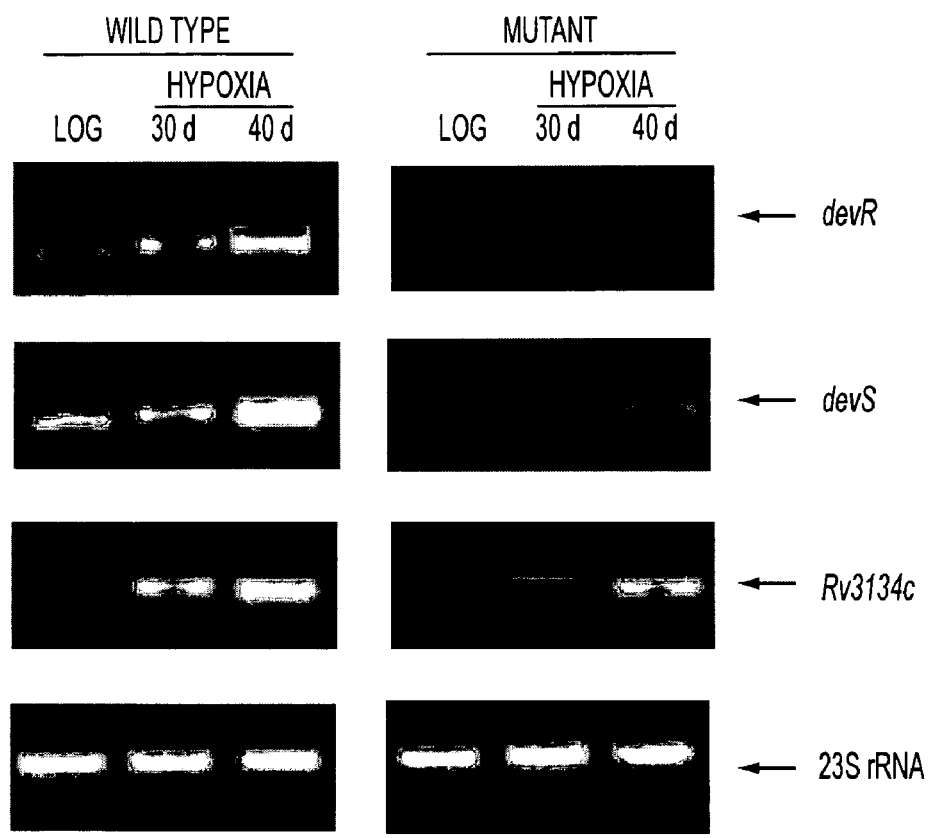

FIG. 2 shows a) Western blot analysis of devR mutant *M. tuberculosis* b) Immuno electron microscopy of devR mutant *M. tuberculosis* c) In vitro morphological analysis of the devR mutant and H37Rv strains of *M. tuberculosis*.

FIG. 3 shows expression analysis of Rv3134c-devR-devS operon in wild-type and mutant strains of *M. tuberculosis*.

FIG. 4 shows characteristics of liver and lung granuloma in guinea pigs infected with devR mutant and H37Rv strains of *M. tuberculosis*

DETAILED DESCRIPTION OF THE INVENTION

As per the process of this invention the devR gene of *M. tuberculosis* is disrupted by allelic exchange using standard technologies. Briefly, the devR gene located in a ~3.3 kb EcoRI-HindIII insert of plasmid pJT53.34 is disrupted with a kanamycin resistance ($Km^R$) gene at a unique PpuMI site. The disrupted devR allele is excised as an ApaI-BamHI fragment and cloned into the corresponding sites of plasmid pJQ200SK constructing pJQ200SkdevR::kan. This plasmid is introduced into *M. tuberculosis* H37Rv by electroporation. Single crossover transformants indicative of plasmid integration are selected on Middlebrook 7H10 agar plates containing 20 μg/ml kanamycin and analyzed by polymerase chain reaction (PCR) for the presence of devR, $Km^R$ and sucrose (sacB) gene sequences. Twenty five $Km^R$ colonies are analyzed and only 6 are positive by PCR for $Km^R$, signifying a high frequency of spontaneous $Km^R$ (~75%). All 6 colonies are positive for sacB PCR indicating the involvement of a single crossover event in the generation of $Km^R$ colonies. Three (of 6) are positive by PCR for the wild-type devR (513-bp) and the devR::kan products (1.8-kb) suggesting that integration of the plasmid-bome devR::kan copy into the *M. tuberculosis* chromosome had occurred. PCR assays using chromosome-flanking primers together with $Km^R$ gene-specific primers suggested that plasmid integration had occurred near the devR or devS locus in one clone. Upon Southern hybridization with the devR probe, two signals of 3.8 kb and ~9.5 kb are obtained in contrast to a single hybridization signal of 3.8 kb obtained in the parental strain. Identical results are obtained using the devS gene as probe (FIG. 1A). Hybridization with the $Km^R$ gene probe highlighted the ~9.5 kb fragment containing the vector backbone resulting from a single crossover recombination event to the left of the $Km^R$ gene in the devR or devS locus. The merodiploid strain containing the wild-type and the disrupted copies of the devR locus is designated as *M. tuberculosis* Dup devR (FIG. 1A).

The allelic exchange event is selected in the second step by growing *M. tuberculosis* Dup devR in middle brook 7H9 medium containing kanamycin (20 μg/ml) and 2% sucrose for 7 days. Serial dilutions are plated on 7H10 medium containing kanamycin (20 μg/ml) and 2% sucrose. A total of 87 $Km^R$ and sucrose resistant ($Suc^R$) transformants are obtained; 31 of these are negative by PCR for wild-type devR gene, 18 of which are positive by PCR for the devR::kan disrupted gene. Sucrose resistance arose from one of two events; the sacB gene is either lost as a result of the resolution (64%) or have accumulated mutation(s) resulting in the loss of function (36%). Allelic exchange is confirmed by Southern hybridization. Briefly, 16 (out of 18) $Km^R$-$Suc^R$ transformants are probed with devR and devS gene probes. A double crossover event occurred in 15 clones leading to the presence of devR::kan copy (5.1 kb hyridization signal) instead of the wild-type devR gene (3.8 kb signal), the mutants having a size increment of 1.3 kb corresponding to the $Km^R$ cassette inserted in the devR locus. Hybridization with the $Km^R$ gene probe confirmed the retention of Km cassette-disrupted devR gene copy on the chromosome. The lack of hybridization with sacB probe established that the gene has lost during resolution of the tandem duplication (not shown). A representative clone is shown in FIG. 1A. One devR knockout clone is randomly selected for further characterization. The gene replacement is also confirmed by PCR (FIG. 1B).

Functional disruption of the devR gene in the mutant is confirmed by Western blotting and immuno electron microscopy using standard procedures. Sonicates of logarithmic phase cultures of *M. tuberculosis* H37Rv, devR mutant and *E. coli* are subjected to denaturing polyacrylamide gel electrophoresis, proteins transferred to nitrocellulose membrane and probed with polyclonal anti-DevR antibody diluted 1:1,000 raised in rabbits against DevR protein of *M. tuberculosis*. Immunoreactivity is assessed using horseradish peroxidase-conjugated donkey anti-rabbit immunoglobulin G and 3,3'-diamino-benzidine substrate. DevR protein is visualized in *M. tuberculosis* H37Rv and in recombinant *E. coli* overexpressing DevR protein but not in the mutant strain (FIG. 2A). By immuno electron microscopy, DevR labelling occurred on the surface and in the cytosol of wild-type organisms (25±2.4 gold grains per bacillus) but not in the mutant strain (2±0.88 gold grains per bacillus, FIG. 2B).

The morphology of mutant and parental bacilli is compared by scanning electron microscopy. Logarithmic phase mutant bacilli are longer in size (average 4-6 μm) in comparison to the wild-type bacilli (average 2-4 μm, FIG. 2C). The growth curves of the devR mutant and parental strains cultured in triplicate under aerobic conditions in 7H9 containing 10% albumin-dextrose and 0.05% Tween 80 are compared. The mean $A_{590}$ increased from 0.054 on day 1 to 1.41 on day 28 with wild-type cultures and from 0.048 on day 1 to 1.9 on day 28 for mutant cultures. The differences in $A_{590}$ at various time points for the mutant and parental strains are not statistically significant (by Wilcoxon Rank Sum test) suggesting that the devR mutation did not have a significant impact on the growth of *M. tuberculosis* under aerobic conditions.

The effect of oxygen limitation on the expression of devR and devS genes of *M. tuberculosis*, shown earlier to be co transcribed in *M. tuberculosis* was assessed. The use of an in vitro model of *M. tuberculosis* dormancy in which the cultures have grown in Dubos Tween Albumin without agitation and slowly descended to the bottom of the culture vessel where the low oxygen concentration limited growth. After ~30 days, the bacteria entered a stationary/nonreplicating growth phase. During this period, the wild-type bacteria grew ~18-fold. The wild-type organisms adapted to gradual oxygen deprivation without a detectable loss of viability. The mutant bacteria grew only ~5-fold over the 30 day period. At the end of the experiment, the viability of the mutant strain is ~25% of that of the parental strain. Aerobic shaker cultures of *M. tuberculosis* parental and mutant strains are grown simultaneously to logarithmic phase ($A_{590}$~0.4). RNA is isolated from logarithmic phase, 30-day and 40-day unagitated cultures using the Rneasy Mini kit (Qiagen, Germany) and RT-PCR analysis is performed for transcripts originating from the Rv3134c-devR-devS operon (Rv3134c is the first gene in this operon). The gels are scanned using the UVP gel documentation system and densitometric analysis is performed using the Labworks™ analysis software (Ultra-Violet product, USA). The expression of devR, devS and Rv3134c genes is up regulated ~3- to 4-fold in wild-type cultures under hypoxic conditions. An up regulation is also observed in the mutant strain except that the basal level of expression of Rv3134c and devS gene is ~2.5-fold lower than that observed in the wild-type strain. As expected, transcripts from the wild-type devR gene are not detected in the mutant strain (FIG. 3). The expression and up regulation of the devS gene in the mutant strain is thought to be due to transcription originating upstream since the expression of the $Km^R$ cassette (within the devR gene) is also up regulated under similar conditions (data not shown).

The process for identifying a novel target for use for the development of therapeutic modalities and anti tubercular drugs is herein described in detail.

The effect of the devR mutation on in vivo growth and the ability to cause disease in guinea pigs is evaluated as described. Albino, random bred guinea pigs (five animals per group) are subcutaneously injected with 0.1 ml of viable bacilli in phosphate-buffered saline (*M. tuberculosis* H37Rv×$10^6$ CFU and devR mutant 3.2×$10^7$ CFU). Guinea pigs were sacrificed 47 days post-infection. One animal (H37Rv group) that died a non-tuberculosis death before the date of sacrifice is omitted from the analysis. The amount of visible tuberculosis in internal organs is scored immediately after sacrifice as described. A heavy involvement of the lungs, liver, spleen and lymph node is noted in the guinea pigs infected with *M. tuberculosis* H37Rv. The visual scores ranged between 43 and 93 (mean 77) and between 23 and 48 (mean 38.4) for guinea pigs infected with the parental and mutant strains respectively, the difference being significant ($p<0.05$). The liver is the most affected organ and heavy invasion with numerous large tubercles and areas of necrosis is seen in guinea pigs infected with the parental strain. Spleen and lungs showed moderate invasion with numerous small tubercles. Considerably less number of visible lesions is seen in the organs of guinea pigs infected with the mutant strain. Spleens are homogenized and serial dilutions are plated on LJ slants. A total of 7.09±0.83 $log_{10}$ cfu are isolated from spleens of animals infected with the parental strain vs. 4.4±1.21 $log_{10}$ cfu recovered from spleens of animals infected with the mutant strain, the difference being significant ($p<0.05$).

Figure 4:
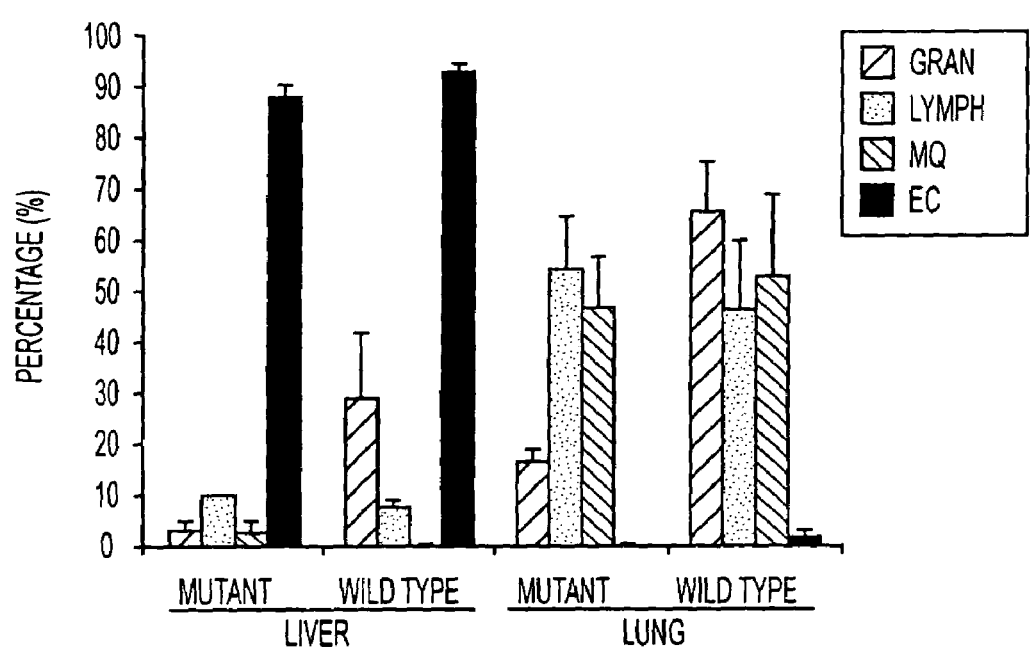

Serial 5 μm sections from the liver and lung autopsy specimens are subjected to a semiquantitative appraisal of the histological features (organ architecture, the percentage area occupied by the granuloma in the section and the percentage of the major cellular components within the granuloma) as described previously. Liver sections from three of five guinea pigs infected with the mutant strain had normal architecture and do not show any granuloma or the presence of inflammatory cell infiltrates. In the remaining two animals infected with the mutant strain, minimal, well-organized, non-necrotic epithelioid cell granuloma is observed. Liver sections from all four guinea pigs infected with the parental strain showed the presence of well-formed granuloma that consisted of epithelioid cells and lymphocytes. Other cell types are absent. In one animal, the granuloma is extensive (65%) and is accompanied by the partial destruction of organ architecture (FIG. 4). In FIG. 4. the acronym "Gran" refers to granuloma; the acronym "Lymph" refers to lymphocytes; the acronym "Mq" refers to macrophages; and the acronym Ec refer to epithelioid. Compared to the liver, much more extensive involvement of the lung is noted. The lung architecture in all the guinea pigs infected with the mutant strain is normal. Although all the animals showed the presence of granuloma, it is minimal and consisted of both lymphocytes and macrophages. Giant cells and other cells or necrosis are not seen in any of the lungs. In animals infected with the parental strain, lung from one guinea pig is completely destroyed and is partially damaged in the remaining three. The granuloma ranged from 40% to 85% and varied from being predominantly lymphocytic to mainly histiocytic (FIG. 4).

At 7 weeks post-infection, significantly less organ pathology is observed and a nearly thousand-fold lower bacterial load are recovered from guinea pigs infected with the mutant strain compared to those infected with the parental strain. The preponderance of epithelioid cells over macrophages and lymphocytes in liver as compared to lung is suggestive of a good immune response and more advanced resolution of granuloma in the former.

Therefore it is seen that the DevR-DevS two-component system is involved in the virulence of *M. tuberculosis* and could well be a key regulatory link between oxygen limitation and the initiation and maintenance of the adaptive response to hypoxia. Mycobacterial adaptation to an anaerobic microenvironment is thought to provide a means for the tubercle bacilli to reside indefinitely in a dormant/stationery phase-like persistent state within inflammatory and necrotic lesions such as granuloma. Therefore this genetic system could serve as a vital target for the development of new and novel drugs for the treatment of tuberculosis particularly the condition of persistence.

We claim:

1. A process for identifying a novel target for use for the development of therapeutic modalities and drugs effective against tuberculosis comprising:
   I) disrupting devR (Rv 3133C) gene located in a ~3.3 kb EcoRI-HindIII insert of plasmid pJT53.34,
   II) constructing pJQ200Skdev::kan from the disrupted devR gene,
   III) introducing said plasmid into *M. tuberculosis* H37Rv,
   IV) selecting single crossover transformants indicative of plasmid integration on Middlebrook 7H10 agar plates containing kanamycin,
   V) analyzing said single crossover transformants by polymerase chain reaction (PCR) for the presence of devR, $Km^R$ and sucrose resistance (SacB) gene sequences,
   VI) subjecting said sequences to the step of Southern analysis with devR probe, devS probe kanamycin resistant gene probe so as to designate *M. tuberculosis* Dup devR containing wild-type and the disrupted copies of the devR locus,
   VII) growing *M. tuberculosis* Dup devR in Middlebrook 7HP medium containing kanamycin and sucrose,
   VIII) subjecting said grown *M. tuberculosis* Dup devR strain into a plurality of plates having Middlebrook 7H10 medium containing kanamycin and sucrose therein so as to obtain kanamycin resistant transformants, thereby obtaining devR mutant strain of *M. tuberculosis*,
   IX) subjecting said grown *M. tuberculosis* devR to the step of Southern hybridization followed by polymerase chain reaction process for the confirmation of said allelic exchange,
   X) subjecting said transformants to the step of polymerase chain reaction analysis for devR::kan disrupted gene,
   XI) subjecting said devR::kan disrupted gene to the step of Western blotting and immuno electron microscopy for the confirmation of functional disruption of said gene, XII) evaluating the viability of growth of the strain *M. tuberculosis* devR mutant under conditions of oxygen limitation for devR and devS gene expression, XIII) evaluating the viability of growth of said strain *M. tuberculosis* devR under conditions of oxygen limitation in aerobic conditions for devR and devS gene expression, XIV) subjecting said grown strain to the step of RT-PCR analysis for transcripts obtained from the Rv3134c-devR-devS operon, XV) scanning said transcripts by using the Ultra-Violet products gel documentation system and subjecting the same to the step of densiometric analysis by using a computer software, XVI) testing *M. tuberculosis* devR mutant strain for virulence in guinea pigs comprising (a) histopathological analysis of the infected organs (lung and liver) from guinea pigs infected with devR mutant and wild-type strains of *M. tuberculosis* and (b) recovery of *M. tuberculosis* from spleen of infected animals and quantification of bacterial load.

2. A process as claimed in claim 1, wherein the said devR allele is disrupted with a kanamycin resistance gene at a unique Ppu MI site.

3. A process as claimed in claim 1, wherein the devR allele is excised as an Apa I Bam HI fragment and cloned into the corresponding sites of plasmid pJQ 200 Sk so as to construct pJQ 200 Sk devR::kan.

4. A process as claimed in claim 1, wherein the plasmid is introduced by electroporation.

5. A devR mutant of *M. tuberculosis*, in which the devR gene is disrupted with kanamycin resistance gene at a unique Ppu M1 site.

* * * * *